(12) United States Patent
White et al.

(10) Patent No.: US 7,377,780 B2
(45) Date of Patent: *May 27, 2008

(54) MEDICAL/DENTAL SUCTION NOZZLE HOLSTER HAVING A HOSE PINCHING DEVICE

(75) Inventors: Lynn R. White, Denver, CO (US); Jeffrey T. Samson, Boulder, CO (US); James V. Osburn, Lafayette, CO (US)

(73) Assignee: Patient Shield Concepts, LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/556,906

(22) Filed: Nov. 6, 2006

(65) Prior Publication Data
US 2007/0057129 A1   Mar. 15, 2007

Related U.S. Application Data

(63) Continuation-in-part of application No. 11/051,649, filed on Feb. 4, 2005.

(51) Int. Cl.
*A61C 13/38* (2006.01)
*A47F 5/00* (2006.01)

(52) U.S. Cl. .................................. 433/77; 248/309.1
(58) Field of Classification Search ............ 433/77–79, 433/91–96; 248/200, 309.1, 311.2, 313
See application file for complete search history.

(56) References Cited

U.S. PATENT DOCUMENTS

| 1,096,180 | A | * | 5/1914 | Meurling ........................ 24/5 |
| 2,689,563 | A | * | 9/1954 | Huber ........................ 604/412 |
| 4,579,309 | A | * | 4/1986 | Fujiwara et al. ......... 248/311.2 |
| 5,224,679 | A | | 7/1993 | Code |
| 5,752,286 | A | | 5/1998 | Wright |
| 5,806,822 | A | | 9/1998 | Schulz |
| 5,915,963 | A | * | 6/1999 | Homra ........................ 433/77 |
| 5,927,974 | A | | 7/1999 | Homra |
| 6,077,074 | A | | 6/2000 | Homra |
| 6,367,110 | B1 | | 4/2002 | Urueta et al. |
| D517,310 | S | * | 3/2006 | Aron et al. .................. D3/218 |
| 2005/0194507 | A1 | * | 9/2005 | White ........................ 248/314 |

* cited by examiner

*Primary Examiner*—John J Wilson
*Assistant Examiner*—Heidi M Bashaw
(74) *Attorney, Agent, or Firm*—Dorr, Carson & Birney, P.C.

(57) ABSTRACT

A suction nozzle holster whose upper rim is provided with a notch into which a suction hose can be forced in order to constrict the hose and, hence, curtail the vacuum conditions in a suction nozzle.

18 Claims, 10 Drawing Sheets

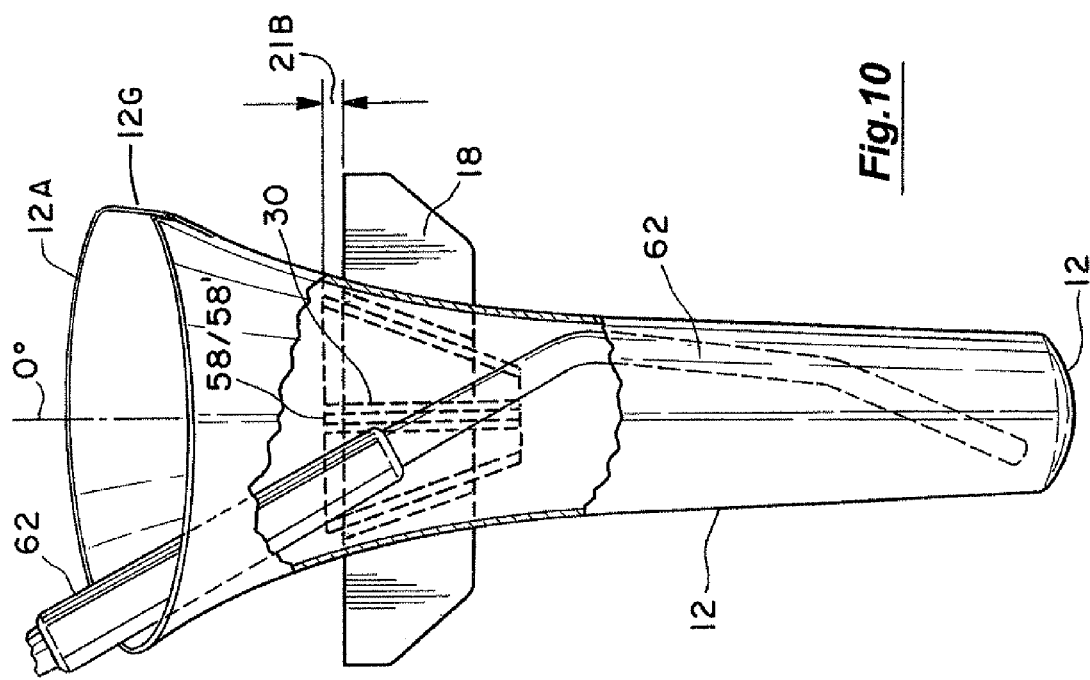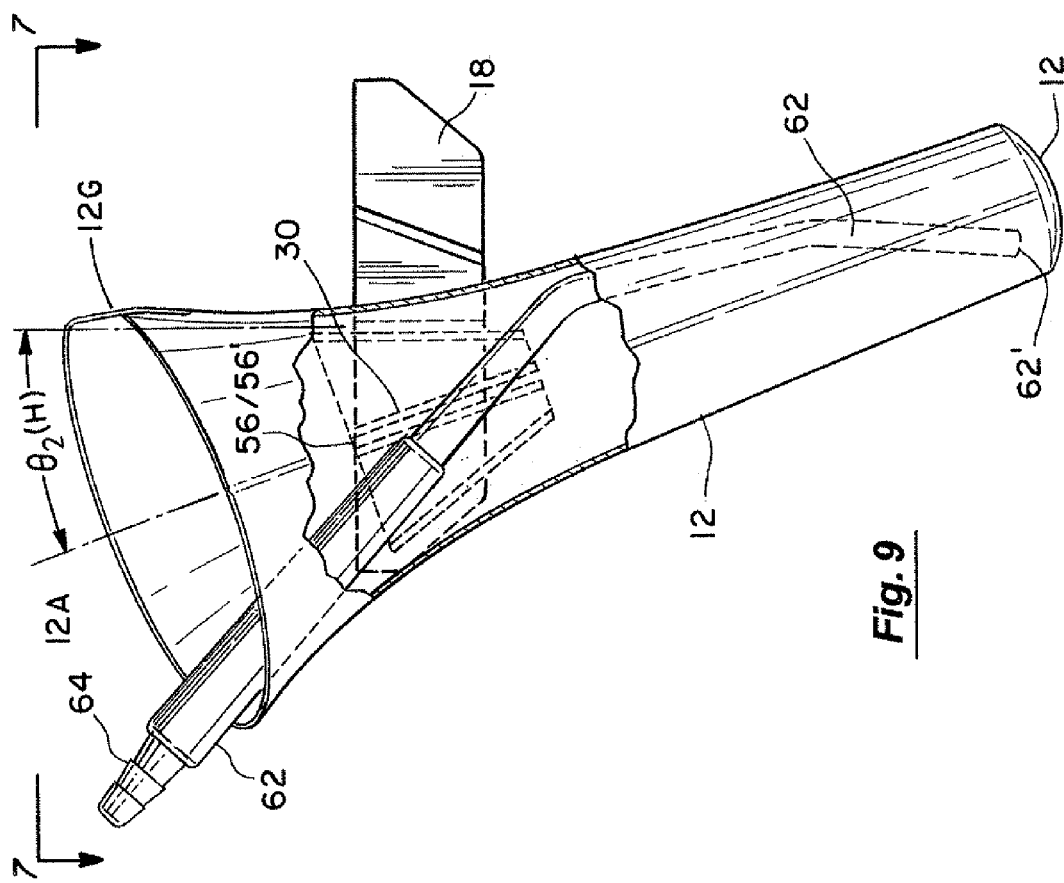

MEDICAL/DENTAL SUCTION NOZZLE HOLSTER HAVING A HOSE PINCHING DEVICE

RELATED APPLICATIONS

This patent application is a continuation-in-part of U.S. patent application Ser. No. 11/051,649 filed Feb. 4, 2005 entitled "Medical/Dental Suction Nozzle Holster."

BACKGROUND OF THE INVENTION

1. Field of the Invention

This invention is generally concerned with holsters for the nozzle components of medical/dental suction devices such as so-called Yankauer suction tubes. The use of Applicant's holsters serves to maintain aseptic conditions and convenient human hand access to such suction devices during medical/dental procedures. This invention is also particularly concerned with providing a means whereby a hose that services suction devices of this type can be pinched off (constricted) to such an extent that the partial vacuum conditions that exist in the hose during medical/dental procedures are substantially curtailed or even completely shut off.

2. Discussion of the Background

A wide variety of prior art medical suction nozzle holsters are disclosed in the patent literature. Such holsters have many different features that perform various distinct technical functions as well as various convenience-in-use functions. These convenience-in-use functions often involve the methods and mechanical devices used to temporarily attach such nozzle holsters to a bedrail or operating table rail for ease and/or convenience of use during medical/dental procedures wherein the medical/dental practitioner's attention is often urgently directed away from such holsters. None of these prior art medical suction nozzle holsters, however, provide a device and/or method for readily curtailing, shutting off, etc. those partial vacuum conditions extant in a flexible hose that leads from the suction device (e.g., a Yankauer suction tube) to a waste fluid disposal container.

For example, U.S. Pat. No. 6,367,110 B1 ("the '110 patent") teaches a holster for an electrocautery tip. The holster is attached to an operating table, Mayo instrument table, etc. by a temporary attachment means such as a spring-loaded, wide-base C-clamp (see FIGS. 4a and 4b) or a releasable clip (see FIG. 4). Since the outwardly-extending member is integral and unitary with the receptacle, there is no way to rotate the receptacle with respect to the outwardly-extending member. No suction hose pinching device is disclosed in this '110 patent.

U.S. Pat. No. 5,752,286 ("the '286 patent") discloses a cleaning and storage device for an aspirator instrument such as a Yankauer suction tube. The device has a holder that can be attached to a bedrail by opposing adhesive surfaces or by a C-shaped clamp. Here again, no suction hose pinching apparatus is disclosed.

U.S. Pat. No. 5,806,822 ("the '822 patent") discloses a wall mounted holder for a Yankauer suction instrument. The holder has a base and two spaced supports respectively extending substantially horizontally from the upper end of the vertically mounted base and from the lower end of said base. The upper support may comprise, for example, a continuous rim that forms an annular ring that defines an opening for receiving the forward end of the suction instrument and thereby preventing it from tipping laterally. The lower support preferably has two spaced support arms that define a substantially horizontal slot. In effect an upper end of the suction device resides in the ring while the handle portion of the suction device rests on the support arms above the slot while a suction hose portion of the suction device extends through the horizontal slot defined by the two spaced apart support arms. No hose pinching device is taught or suggested.

U.S. Pat. No. 6,077,074 ("the '074 patent") discloses a sleeve-type holder for a suction device such as a Yankauer suction tube. One end of a sleeve component of this holder is provided with a frame that can be slidably mounted to a C-shaped frame track having a compatible C-shaped channel configuration. The opposing end of the sleeve is provided with a hole for receiving a hook of a body member bar. The body member bar is attached to a clamp that attaches the bar, frame and sleeve assembly to a bedrail. Thus, the sleeve that holds the suction tube can not be rotated once the frame is inserted into the channel portion of the C-shaped frame track. No hose pinching apparatus is disclosed.

The teachings of U.S. Pat. No. 5,927,974 ("the '974 patent") are quite similar to those of the '074 patent. It does, however, contain the added feature (see FIGS. 10 and 11) of providing the frame with a dovetail side that is inserted into a dovetail track (i.e., dovetail-shaped channel). Such an arrangement does not permit rotation of the sleeve with respect to the dovetail tracks channel portion. No hose clamping or constricting device is taught or suggested.

The teachings of U.S. Pat. No. 5,915,963 ("the '963 patent") are similar to those of the '974 patent. The main difference between these two patent references is depicted in FIGS. 17 and 18 of the '963 patent. They show a frame-like member hingedly mounted to a mounting plate. This plate is fixedly mounted to a clamp that is, in turn, slidably mounted to a bedrail or similar bar-like object. This construction does not permit vertical rotation of the sleeve to any alternative position or orientation. Nor does this apparatus provide for pinching off a hose leading from a suction device to a waste disposal unit.

U.S. Pat. No. 5,224,679 ("the '679 patent") teaches a holster for a hand-held instrument such as an intake nozzle of an operating room suction device. The '679 patent suggests several ways the holster may be attached to an operating table (see FIGS. 1, 4 and 5). These ways include: (a) blade-like inserts for placement between table tops and cushions, alligator clamps and C-clamps having hand operable tightening/loosening bolts. This holster is adapted to hold a bubble wrap in which the suction device was originally packaged. The suction tip is holstered in this original package during use. The nozzle holster also is adapted to secure the bubble wrap to the inside of the holster. After the operation is over, the wrapper and nozzle are disposed of and a new nozzle-containing wrapper (e.g., clear plastic bag) is put in the holster. Here again, no hose pinching apparatus is taught or suggested.

It might also be noted that not only do these prior art devices fail to provide a convenient means of curtailing the suction conditions in their respective suction tubes, none of them allow for variation in the vertical orientation of the handle of the suction nozzles held in such holsters. The hereinafter described medical/dental suction nozzle holsters of this patent disclosure not only provide a means for curtailing suction conditions in a suction tube, they also address the need for variation in the vertical orientation of a nozzle handle. They do this by providing three separate and distinct vertical orientations for the holster.

SUMMARY OF THE INVENTION

The medical/dental suction nozzle holster devices of this patent disclosure are particularly characterized by the fact that they have at least one vertical constriction such as a Y-shaped notch or V-shaped notch in the upper rim of their holster component. The top of a given notch will be wide enough (e.g., from about 0.5 to about 2.0 inches) to accept the outside diameter of commonly available suction hoses and then generally get progressively more narrow as they descend downward in the body of a holster. In effect, such a notch will provide a generally Y-shaped or V-shaped configuration that progressively becomes more and more narrow or constricted in its lower regions. That is to say that the upper regions of these notches should readily admit the outside diameter of such hoses while the lower regions of said notches will be constricted to a degree that the inside diameter region of a flexible and compressible hose will be substantially pinched together as the hose is forced downward in the notch and thereby curtail air/fluid flow through the hose. Generally speaking, the vertical depth of the notch generally should not exceed more than about one fourth of the vertical depth of the holster body. Notches having vertical depths of from about 1.0 inches to about 3.0 inches will generally suffice.

The ability of a medical/dental practitioner to curtail the suction action at the holster—as opposed to turning a shut off valve on a vacuum creating device (aspirator) that is typically located much further away from the patient—has a great deal of convenience-in-use value. That is to say that the notch in the holster enables the practitioner to more conveniently shut off the suction action while said practitioner's attention is still directed toward a nearby patient. There also may be times during the course of an operation that the medical staff need to converse in a relatively calm, quiet atmosphere. Because suction tubes make clearly discernable sucking or aspirating sounds that are annoying, distracting and/or not conducive to quiet conversations, it is of considerable advantage to have the ability to temporarily eliminate such sounds without having to leave the immediate vicinity of the patient to turn a shut off valve at the aspirator device.

Next, it should be noted that Applicant's notched holster can be attached to a convenient anchor point (e.g., an operating table rail, bed rail, stand, wall attachment, etc.) by anchor devices (e.g., c-clamps, alligator clips, set screws, etc.) such as those disclosed in the previously discussed prior art patents. However, notched holster devices that have three separate and distinct operating positions will provide certain added advantages. For example, each different operating position will provide a means for placing the holster device—and hence, the medical/dental suction nozzle that the device holds—in an operating position that a medical/dental practitioner may find relatively more convenient and/or practical. They can be, for example, more readily adapted for use by left-handed as well as right-handed practitioners. Moreover, such holster devices can be readily changed back and forth between their three possible operating positions without the use of hand tools or hand tightening knobs that operate bolts and the like—that sometimes unexpectedly loosen during use in medical/dental operations.

These three positions are made possible through selective use of two main components. The first main component is a holster component that in addition to having at least one notch in its upper rim also have a holster mounting mechanism that further comprises a rear plate having a keyway slot/nub receiver opening system. The second main component is a mounting channel component. The mounting channel component provides the means by which the operating position of the holster component can be initially selected and/or changed. To these ends, the face side of a front vertical plate of the mounting channel is provided with three separate and distinct key plate/key nub systems. Each of these key plate/key nub system may be readily inserted into (or removed from) the keyway slot/nub receiver opening system located in the rear plate of the holster mounting mechanism.

For example, insertion of a left key plate/key nub system into the keyway slot/nub receiver opening system in the rear plate of the holster mounting mechanism causes the holster to be firmly held in a leftward tilting operating position. Thus, the handle of a suction nozzle placed in the holster also has a leftward tilting orientation. Conversely, insertion of a right key plate/key nub system into the keyway slot/nub receiver opening system in the rear plate of the holster mounting mechanism causes the holster (and hence the nozzle it holds) to be held in a rightward tilting operating position. Placement of the center key plate/key nub system in the rear plate's keyway slot/nub receiver opening system will cause the holster (and nozzle handle) to hang in a substantially vertical orientation.

Applicants' suction nozzle holster device has various other features of note. For example, the mounting channel component further comprises a rear vertical plate that is attached to the rear side of the front vertical plate by means of a horizontal ledge that connects the two vertical plates. This horizontal ledge also serves as the top surface of a bottom mounting channel region in which a rail (e.g., an operating table rail) resides. The rear side of the vertical channel forms one side wall of the bottom mounting channel region while the front side of the rear vertical plate forms the other side wall of the bottom mounting channel region.

Next, it should be noted that an upper part of the rear vertical plate projects above the intersection of the horizontal ledge with the rear vertical plate while a lower part of the rear vertical plate projects below the horizontal ledge/rear vertical plate intersection. In effect, the inside surface of the upper part of the rear vertical wall serves as the front side of the rear vertical plate that forms the other side wall of the bottom mounting channel region. As will be better seen in FIG. 9, the lower part of the rear vertical plate serves as a lever arm used to lower the upper part of the rear vertical plate. To this end, the outside surface of the lower part of the rear vertical plate can be further provided with a surface suitable for human thumb/finger contact. For example this surface can be given a roughened surface to prevent thumb/finger slippage from this outside surface of the lower part of the rear vertical plate. The lower end of the rear vertical plate also can be provided with a projecting ledge or extended nub to facilitate human thumb/finger gripping of the lower part of the rear vertical plate. These thumb/finger contact enhancing features are not essential to the use of this medical/dental suction nozzle holster device, but they are very practical optional features. This follows from the fact that the holster device is often mounted to a side rail (and dismounted from such a rail) by hands residing in wet surgical gloves.

BRIEF DESCRIPTION OF THE DRAWINGS

FIG. 9 is a partially cut-away view of the medical/dental suction nozzle holster device holding a Yankauer suction tube at a leftward tilting angle $\theta_2(H)$.

FIG. 10 is a partially cut-away view of the medical/dental suction nozzle holster device mounted in a substantially vertical orientation.

DETAILED DESCRIPTION OF THE INVENTION

Figure 1:
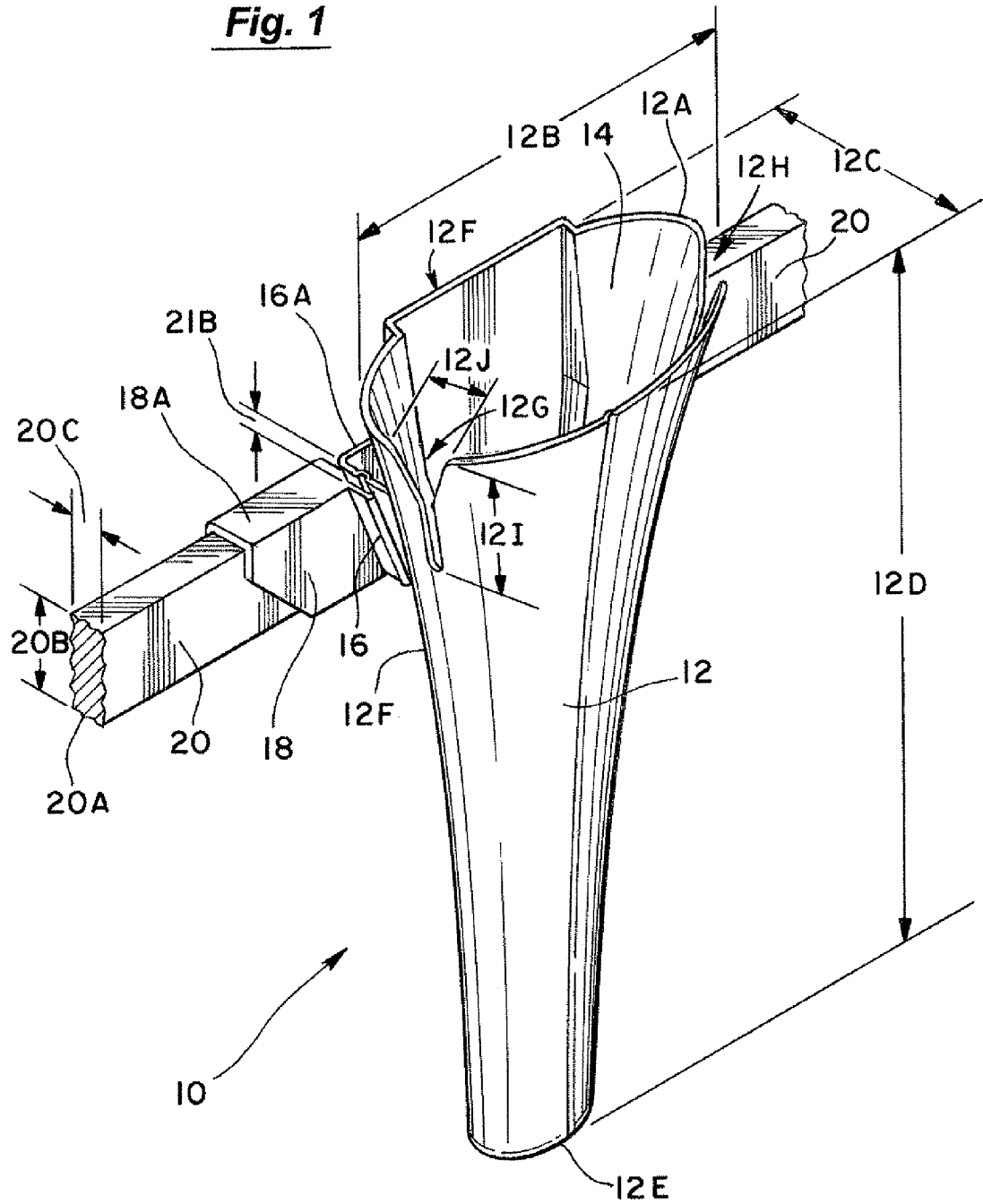
FIG. 1 is a perspective view of a medical/dental suction nozzle holster device of this patent disclosure mounted to a rail (e.g., the side rail of an operating table).

FIG. 1 depicts a medical/dental suction nozzle holster device 10 made and assembled according to certain teachings of this patent disclosure. This holster device 10 has a holster component 12 that generally defines an inwardly and downwardly constricted holster cavity 14 for receiving a front end of a suction nozzle e.g., a medical suction nozzle of the Yankauer type (not shown). The top lip 12A of the holster component 12 is shown in FIG. 1 as having a generally elliptical configuration. The long diameter 12B of such an elliptical configuration will preferably be from about 3 to about 6 inches (and more preferably from about 4-5 inches). The short diameter 12C of the elliptical configuration will preferably be from about 1.5 to about 3 inches (and more preferably from about 1.5 to about 2.0 inches). The holster component 12 will have a depth 12D that will preferably range from about 5.0 to about 13 inches (and more preferably from about 9.0 to about 11.0 inches). The body of the holster component 12 is shown generally tapering downwardly and inwardly to a closed, elliptically shaped, closed bottom 12E. The long diameter of this elliptically shaped, closed bottom 12E will be from about 1.0 to about 2.0 inches (and preferably from about 1.25 to about 1.75 inches) while its short diameter will be from about 0.5 to about 1.0 inches (and preferably from about 0.75 to about 1.0 inches). The top lip 12A and/or the closed bottom 12E could have other geometric configurations (e.g., circular, rectangular, square, etc.), but applicant has found that elliptical configurations such as that depicted in FIG. 1 are preferred in that they generally facilitate more accurate human hand placement of suction nozzles in such a holster cavity 14 during the course of medical/dental procedures.

The top lip 12A of the holster 12 is shown provided with two separate and distinct notches 12G and 12H. These notches are shown having a generally Y-shaped configuration (a V-shaped notch also may be employed). In either case, the depth 12I of notch 12G (as well as the depth of notch 12H) will generally be less than one quarter of the depth 12D of the holster. For example, depth 12I will generally be from about 1.0 to 3.0 inches. The width 12J of the top of the notch will generally be from about 0.5 to about 2.0 inches.

FIG. 1 also illustrates an embodiment of this invention wherein the holster component 12 further comprises a holster mounting mechanism 16 affixed to the rear side 12F of the holster component 12. This holster mounting mechanism 16 can be fixedly, but detachably, attached to a mounting channel 18 that, in turn, is slidably attached to a rail 20. FIG. 1 shows the mounting channel 18 partially encompassing such a rail 20 (e.g., a rail of the type commonly found on the sides of operating room tables). Such rails often have certain standardized cross sections 20A. For example, many rails commonly found on operating room tables are rectangular in nature and have a height 20B of about 1.25 inches and a width 20C of about 0.3125 inches. Other rail dimensions and cross section geometries (e.g., circular. square, etc.) are of course also possible. FIG. 1 also depicts a gap distance 21B between the top surface 18A of the mounting channel 18 and a top surface 16A of the holster mounting component 16. The cause and significance of this gap distance 21B will be discussed in ensuing discussions of FIGS. 7, 8 and 10.

Figures 2, 2A:
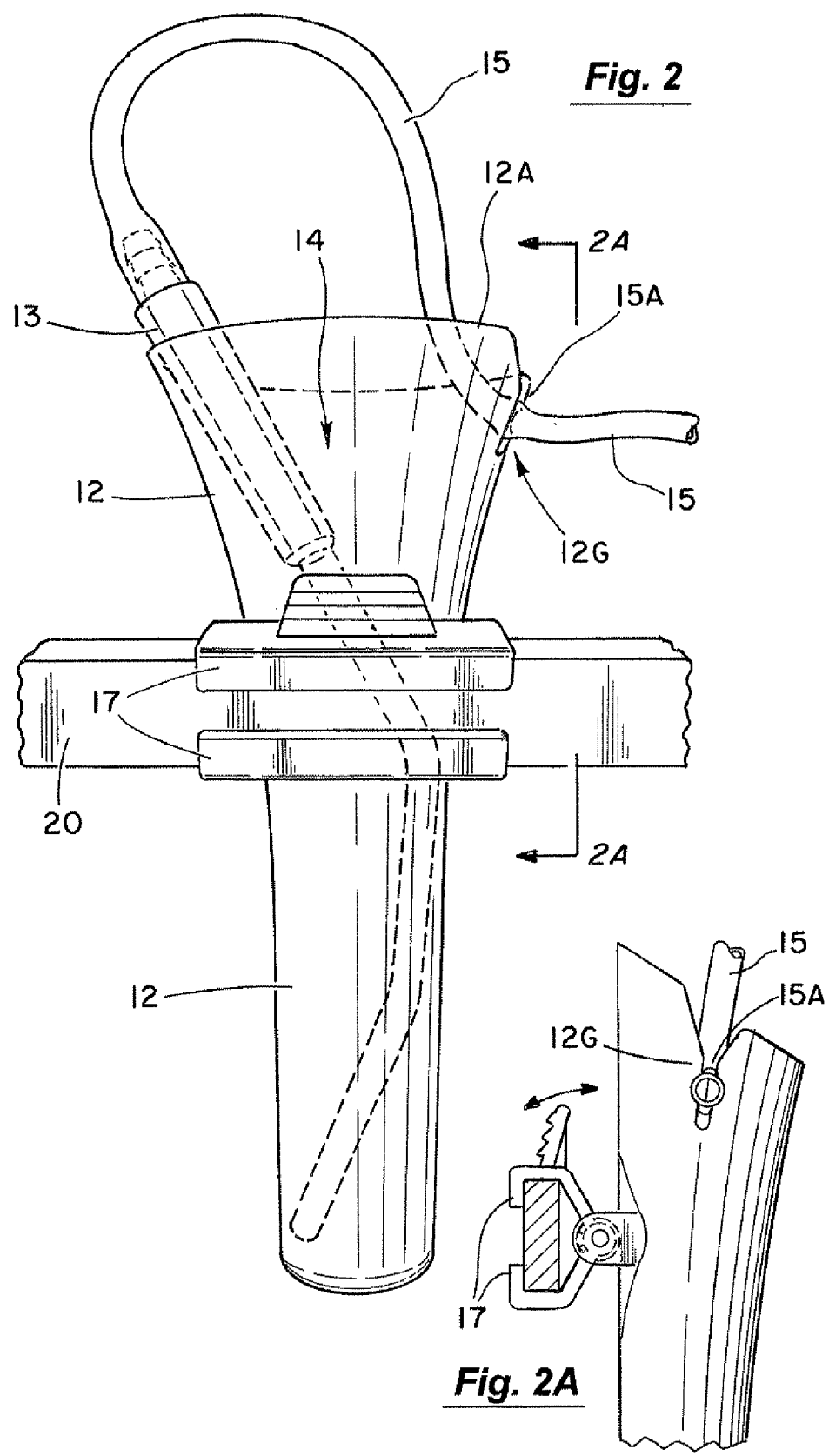
FIG. 2 is a side perspective view of a holster having a notch that is being used to pinch a suction hose leading to a suction tube residing in the holster.
FIG. 2A is a cross section view taken along section lines 2A-2A of FIG. 1.

FIG. 2 depicts a suction tube 13 residing in a holster cavity 14. The top or handle end of the suction tube 13 is shown attached to a flexible and compressible hose 15 of the type commonly used in conjunction with medical/dental suction tubes. Such hoses are connected to a suction device (not shown) that serves to create partial vacuum conditions at the lower end of the suction device and thereby serve to suck fluids from a patient's mouth, throat, stomach, etc. Such suction devices are commonly located away (e.g., 5-10 feet) from the patient.

In this view the rim 12A of the holster is shown provided with a single, Y-shaped, notch 12G. Again, a V-shaped constriction can also be employed to constrict a suction hose. A portion of the hose 15 is shown pushed downward into the lower regions of such a notch 15. This action serves to create a constricted region 15A in the hose and thereby curtailing, shutting off, etc. the vacuum conditions in the hose—and hence in the suction tube serviced by that hose. By way of example only, this particular holster is shown attached to a rail 20 by means of a C-clamp 17 such as that disclosed in U.S. Pat. No. 6,367,110 B1.

FIG. 2A is a cross section view of section 2A-2A of FIG. 2.

Figure 3:
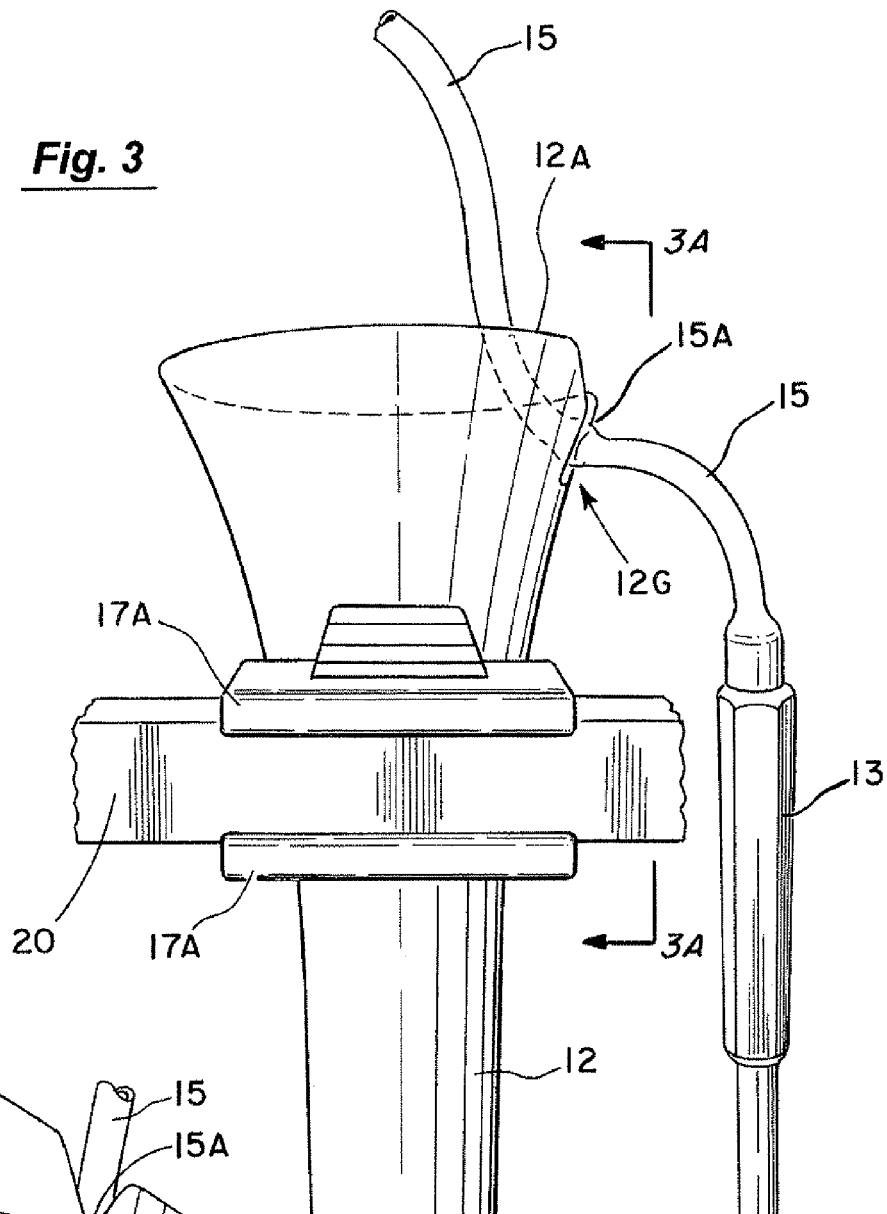
FIG. 3 is a side perspective view of a holster having a notch that is being used to pinch a suction hose leading to a suction tube that is hanging outside of the holster.

FIG. 3 depicts an alternative method of use of this invention wherein a holster 12 having a single Y-shaped notch 12G is shown pinching a hose 15. A suction tube 13 is shown hanging from the hose 15. By way of a further example, this holster 12 is shown attached to a rail 20 by means of so-called alligator clamps 17A.

Figure 3A:
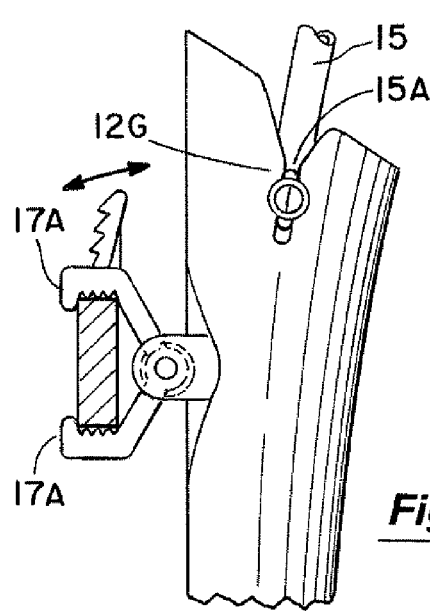
FIG. 3A is a cross section view taken along section lines 3A-3A of FIG. 3.

FIG. 3A is a cross section view of section 3A-3A of FIG. 3.

Figure 4:
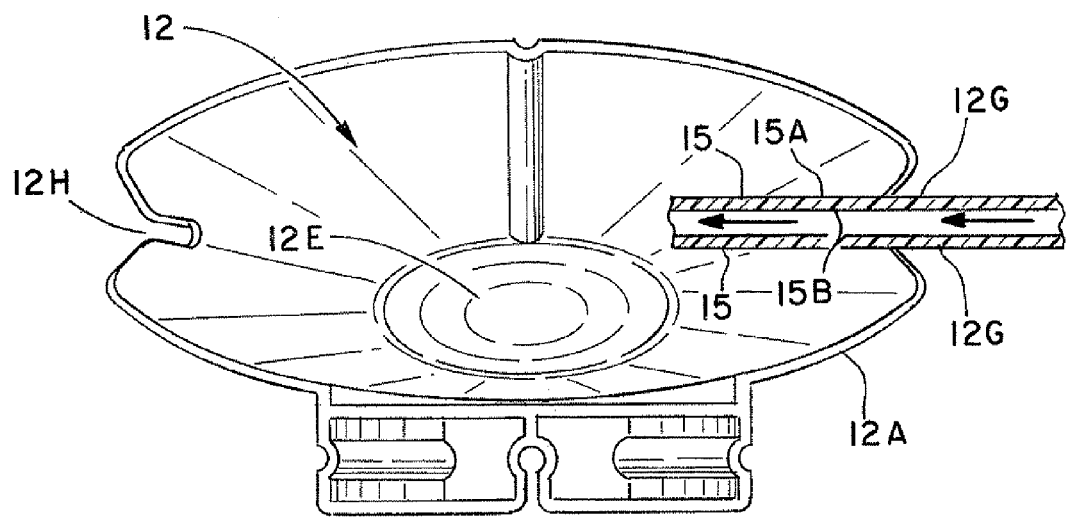
FIG. 4 is a top view of a holster having a notch that is about to receive a portion of a suction hose.

FIG. 4 is a top plan view of a holster 12 having a top rim 12A. This holster is shown provided with two notches 12G and 12H. Notch 12H is shown about to receive a suction hose 15. The hose 15 has an outside surface 15A and an inside surface 15B. In FIG. 4, the hose is just about to enter the notch 12H and therefore has not yet been constricted by the lower, more narrow portions, of said Y-shaped notch.

Figure 5:
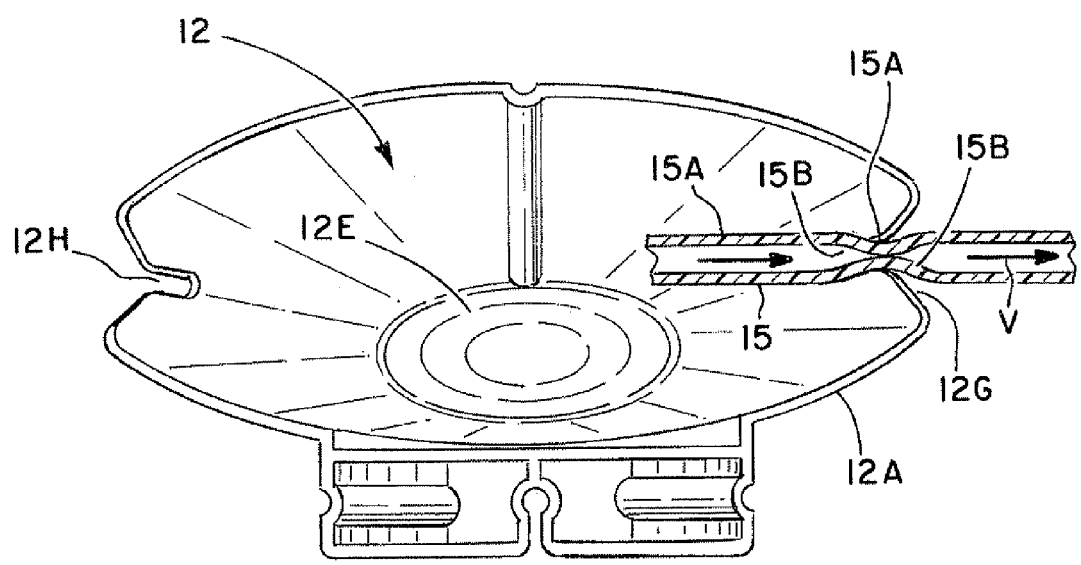
FIG. 5 is a top view of a holster having a notch into which a suction hose has been forced downward and thereby constricting the hose.

FIG. 5 is a top plan view of a holster 12 having a top rim 12A. In effect, this holster is the same as the holster 12 shown in FIG. 4. In this FIG. 5, however, the hose 15 is shown as having been forced downward into the lower regions of the notch 12H. This has caused the outside surface 15A and the inside surface 15B of the hose to be constricted to such an extent that the opposing inside surfaces 15B of the hose are forced into contact with each other and thereby curtailing or completely shutting off the vacuum conditions in the hose that lie to the left of the notch 12H. The ability to easily curtail, partially shut off, totally shut the vacuum conditions in the hose—and hence the suction tube—provide the previously noted benefits to the medical practitioner.

Figure 6:
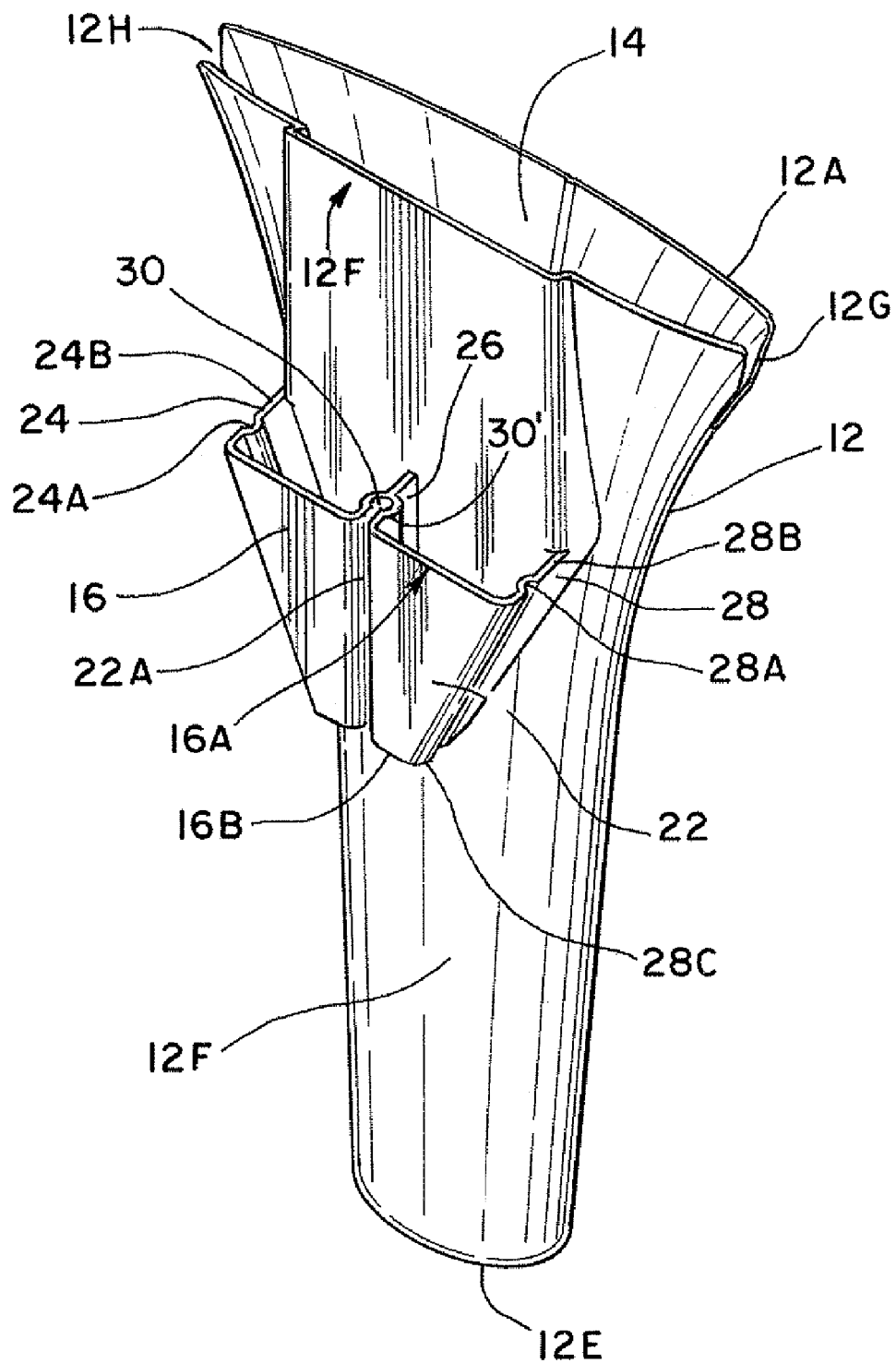
FIG. 6 is a rear perspective view of a holster component of the device.

FIG. 6 depicts a rear perspective view of the holster component shown in FIG. 1. Again, the rear side 12F of said holster component 12 has a holster mounting mechanism 16. This mechanism 16 is in the form of a rear plate 22 that is separated from the rear side 12F of the holster component 12 by three separation ribs, i.e., a right separation rib 24 ("right"—as viewed from the front of the holster e.g., as seen in FIG. 1), a center separation rib 26 and a left separate rib 28. The right separation rib 24 is shown provided with a groove 24A that runs from the top 24B of said right separation rib 24 to its bottom. Similarly, the left separation rib 28 has a similar groove 28A that runs from the top 28B to the bottom 28C of said rib 28. The rear plate 22 of the holster mounting component 16 also is shown provided with a keyway slot 22A that extends from the top 16A of the rear plate 22 to its bottom 16B. The inner regions of this keyway slot 22A lead into a nub receiver opening 30 and thereby defining a keyway slot/nub receiver opening system (the combined 22A/30 opening system). It might also be noted that the rear surface of the nub receiver body 30' is reinforced by the center separation rib 26.

Figure 7:
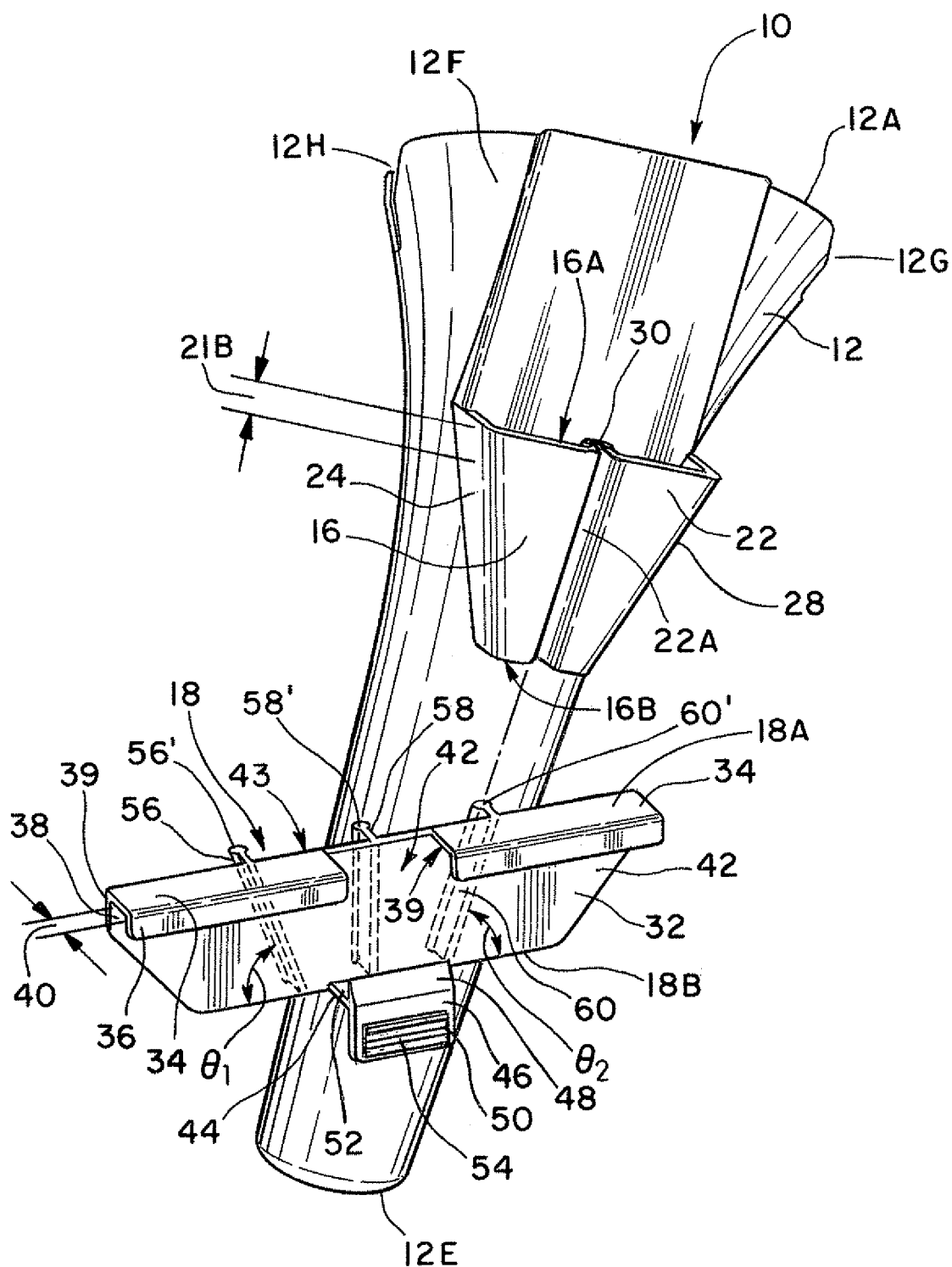
FIG. 7 is another rear perspective view of the holster component as well as the channel mounting component.

FIG. 7 is another rear perspective view of the holster device 10. Here again the rear side 12F of the holster component 12 is shown provided with the holster mounting mechanism 16. This view also shows that the holster mounting mechanism 16 is further provided with a rear plate 22 and that this plate also contains a keyway slot 22A that leads into the nub receiver opening 30 and thereby defining the combined 22A/30 opening system. In a particularly preferred embodiment of this invention, the holster body 12, its holster mounting mechanism 16 as well as the separation ribs 24, 26 and 28 are all unitary in nature owing their being so formed by injection molding of a unitary holster body/mounting mechanism/rib system by a plastic molding operation.

The mounting channel 18 is also shown in perspective in FIG. 7. This mounting channel 18 has a front vertical plate 32, an upper horizontal ledge 34 and an upper rear vertical plate 36 that are so adapted and arranged that they form a top channel opening 38. This top channel opening 38 will have an inside width 40 large enough to accommodate the width of a mounting rail such as that depicted as item 20C in FIG. 1. The rear side of the front vertical plate 32 of the mounting channel 18 is shown attached to one end of a lower horizontal ledge 44. The other end of the horizontal ledge 44 is connected to a rear vertical plate 46. This horizontal ledge 44 also serves as a base component of a bottom mounting channel (see item 41 of FIGS. 12 and 13). A top portion 48 of the rear vertical plate 46 resides above the lower horizontal ledge 44 and a bottom portion 50 of said rear vertical plate 46 resides below the lower horizontal ledge 44. The top portion 48 forms a side of the bottom mounting channel. The bottom portion 50 of the rear vertical plate 46 serves as a lever arm useful in bending the top portion 48 downward to facilitate attachment of the mounting channel 18 to a rail (e.g., rail 20 of FIG. 1). In effect a lower channel region 52 is temporarily taken out of its channel forming configuration. And here again, the various subparts of the mounting channel 18 are preferably unitary in nature owing to their being simultaneously formed by an injection molding process.

Figure 12:
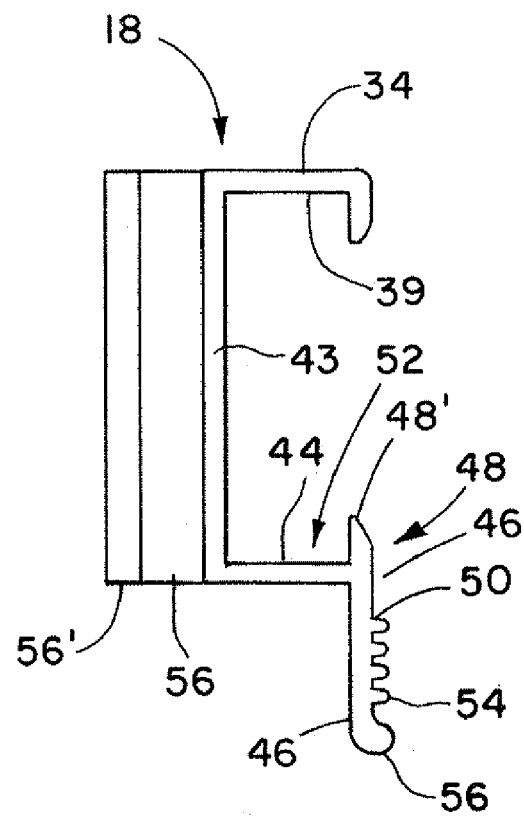
FIG. 12 is a side view of the channel mounting component in its normal operating configuration.
Figure 13:
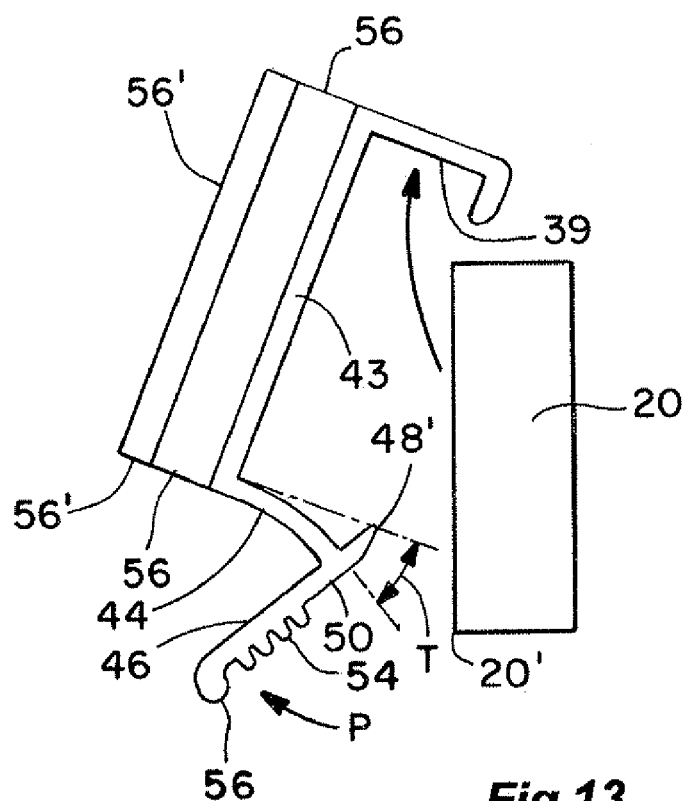
FIG. 13 is a side view of the channel mounting component whose lower horizontal ledge is bent downward to facilitate mounting this component to a rail.

As will be better illustrated in FIGS. 12 and 13, the distance between the underside 39 of the upper horizontal ledge 34 and the top surface of the lower horizontal ledge 44 should be sufficient to accommodate the height of a rail such as that depicted by item 20B in FIG. 1. Similarly, the inside width 40 of the upper channel 38 should be sufficient to accommodate the width of a rail such as the width depicted as item 20C in FIG. 1. FIGS. 12 and 13 also will better illustrate how the top portion 48 of the rear vertical plate 46 can be temporarily bent downward when a substantially horizontally directed human thumb/finger pressure (as suggested by item P of FIG. 8) is applied to the bottom portion 50 of the rear vertical plate 46, This bottom portion 50 of the rear vertical plate is optionally provided with a roughened surface 54 to facilitate such a pressing action. Such a temporary lowering of the top portion 48 of the vertical plate 18 will facilitate placement of the mounting channel 18 around the lower portions of a mounting rail (again, see FIG. 13). This bending action will be facilitated by the fact that the mounting channel 18 also is a unitary piece of suitably elastic, plastic material made by a plastic molding operation.

Next, it should be noted that the face side 43 of the vertical plate 32 is shown provided with a right side key plate 56 (again, as seen from the front of the holster, as in FIG. 1), a center key plate 58 and a left side key plate 60. These key plates 56, 58 and 60 respectively terminate in substantially circularly configured key plate nubs 56', 58' and 60'. Each of these nubs 56', 58' and 60' are capable of being fit into and residing in the nub receiver opening 30 located in the center of the rear plate 22 of the holder mounting mechanism 16. It also should be noted that the right key plate 56 slopes downward and inward (i.e., toward the center key plate 58) at an angle $\theta_1$, the center key plate 58 is substantially vertical and the left key plate 60 slopes downward and inward toward the center key plate at an angle $\theta_2$. These angles $\theta_1$ and $\theta_2$ can be the same angle or different angles. Preferably, both $\theta_1$ and $\theta_2$ will be from about 45° to about 65° with respect to horizontal. A particularly preferred arrangement is one in which $\theta_1$ equals $\theta_2$ and these angles are each about 60° with respect to horizontal.

Figure 8:
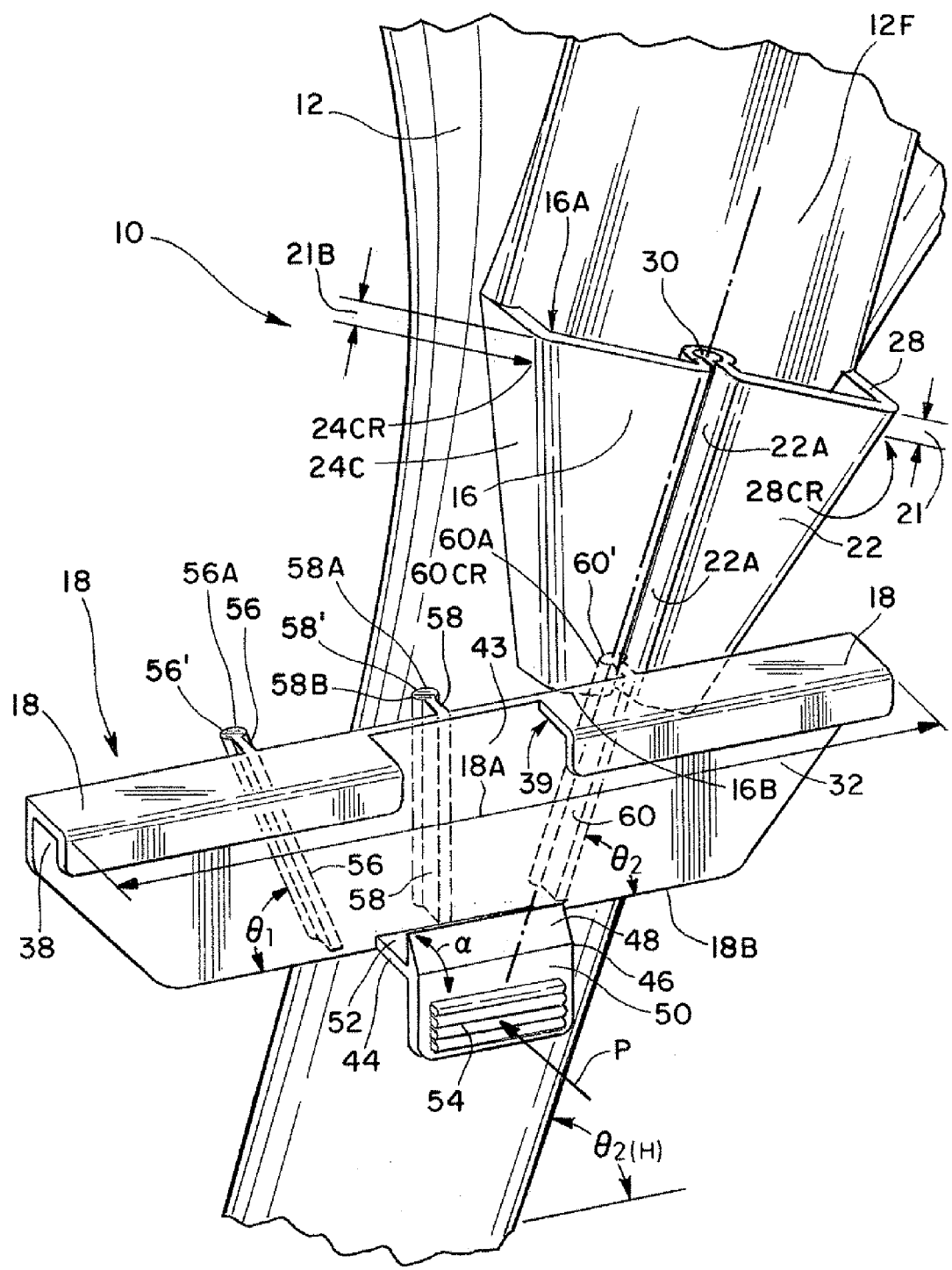
FIG. 8 is yet another rear perspective view showing the holster component and channel component being mechanically coupled to create one of the three possible operating positions of the holster.

FIG. 8 depicts one of the three separate and distinct ways in which the holster component 12 can be combined with the holster mounting channel 18 in order to securely place the holster component 12 in one of its three possible mounting angles ($\theta_2$, vertical or $\theta_1$). In this view, the left nub 60' and its associated left key plate 60 are shown respectively entering the bottom of the nub receiver opening 30 and key slot 22A in the rear plate 22 of the holster mounting mechanism 16. As the holster component 12 is lowered downward, the left nub 60' and its associated left key plate 60 move higher and higher in the keyway slot 22A/nub receiver opening 30 system. Eventually an inside region 58A of the nub 58' of the center key plate 58 collides with a contact region 24CR on the outside surface 24C of the right separation rib 24. This collision prevents the holster component 12 from going further downward and thereby securely holding said holster component 12 in its first operating position. Preferably this collision will also occur in the groove 24A (see FIG. 6) of the right separation rib 24. This collision of the contact region 24CR of the right separation rib 24 and the inside region 58A of the nub 58' of the key plate 58 will take place below the top lip 16A of the rear plate 22 of the holster mounting component 16. Thus a gap 21B is depicted between the contact region and the top lip 16A of the rear plate 22 to illustrate the stopping effect of this right rib contact region 24CR/nub region 58A collision, Since the left nub 60'/left key plate 60 system is in effect mounted at an angle $\theta_2$ with respect horizontal, the holster component 12 will be mounted at a comparable angle $\theta_2$ (H) with respect to a horizontal rail such as the rail 20 depicted in FIG. 1.

Placement of the center key plate 58 and its associated nub 58' in the key slot 22A/nub receiver 30 opening system will cause the resulting key/opening system (and hence the holster component 12) to be in a substantially vertical orientation such as that depicted in FIGS. 1 and 10. This vertical orientation of the holster component 12 constitutes its second operating position. In this vertical orientation, an inside region 56A of the right nub 56' of the right key plate 56 collides with the contact region 24CR of the right separation rib 24. Similarly, an inside region 60A of the nub 60' will collide with a contact region 28CR of the left separation rib 28. These two collisions also create a gap 21B between the top lip 16A of the rear plate 22 of the holster mounting component 16 and the top surface 18A of the mounting channel 18 (see also gap 21B of FIG. 1). In effect this gap 21B indicates that the holster component 12 has been lowered on to the mounting channel 18 as far down as it is intended to go. FIG. 8 designates the horizontal length of the mounting channel 18 as 18A. This length 18A will generally be from about 3 inches to about 7 inches and preferably be about 4.0 to 5.5 inches. The vertical height (from 18A to 18B) of the mounting channel 18 will generally be from about 1.0 inches to about 1.5 inches and preferably from about 1.0 inches to about 1.25 inches.

The third possible operating position of this holster device 10 is achieved when the right key plate 56 and its associate nub 56' are inserted into the key slot 22A/nub receiver 30 opening system in the rear plate 22 of the holster mounting channel 16. In this third operating position, a contact region 58B of the nub 58' of the center key plate 58 will collide with a contact region 28CR of the left separation rib 28. This arrangement will cause the holster to be oriented at an angle comparable to angle $\theta_1$ of the right key plate 56. This orientation is, in effect, the opposite orientation to that illustrated in FIG. 9. Thus, these three possible operating positions provide medical/dental practitioners with three distinct and well secured holster positions. Moreover, these three well secured holster positions can be readily changed from one operating position to another without the need for hand tools or tightening knobs of the type found in the prior art.

FIG. 9 depicts the holster component 12, in a partial cut-away view, in its first operating position, i.e., mounted at an angle $\theta_2$ (H) as a result of the holster's key slot 22A/nub opening 30 system being lowered downward on to the left key plate 60/nub 60' system. FIG. 9 also depicts a typical suction tube 62 and its suction hose coupling device 64. The bottom 62' of the suction tube 62 may or may not come into contact with the holster bottom.

FIG. 10 shows the holster component 12 in its second or vertical operating position. The results from the fact that the center key plate 58/nub 58' system now resides in the key slot 22A/nub receiver 30 system.

Figure 11:
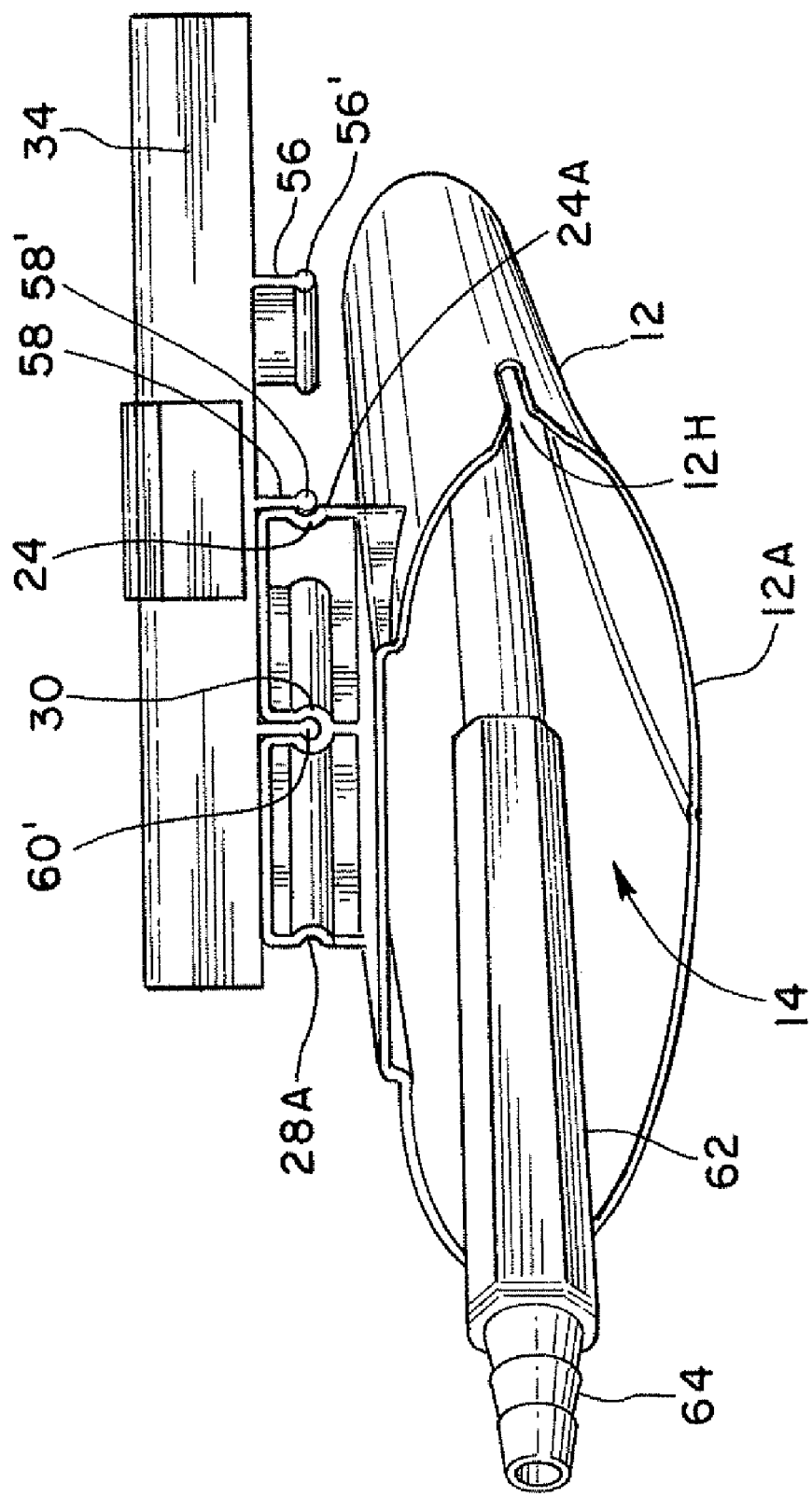
FIG. 11 is a top view of the holster device holding a Yankauer suction tube in the leftward tilting angle $\theta_2(H)$ depicted in FIG. 5.

FIG. 11 is a top view of the holster component 12 mounted on the mounting channel 18. In this top view the left nub 60' is shown occupying the nub receiver opening 30 located on the rear plate 22 of the holster mounting component 16. The center nub 58' is shown in colliding contact with the groove 24A of the right separation rib 24.

FIG. 12 is a side view of mounting channel 18. In this view the lower horizontal ledge 44 is in its normal (i.e., unbent) operating position (i.e., mounted to a rail—not shown). FIG. 12 also shows the outside surface of the low part 50 of the rear vertical plate 46 provided with a rough surface 54 and a bottom nub 56.

FIG. 13 depicts the lower horizontal ledge 44 bent downward at an angle T. This bending action can be created by a pressure P delivered by a human thumb and/or finger(s) (not shown). This allows the tip 48' of the top 48 of the rear plate 46 to pass under the lower, inside corner 20' of the rail 20. When the thumb/finger pressure is released, the lower horizontal ledge 44 returns to its original position (as shown in FIG. 12) and thereby holding the mounting channel 18 to the rail 20. This return is facilitated by the lower horizontal ledge 44 having an elastic quality and "memory" for its original shape.

Those skilled in this art will appreciate that many other features can be employed in the practice of this invention; consequently the preceding patent disclosure should be regarded as illustrating, but not limiting, the scope of the following claims.

Thus having disclosed our invention, what is claimed is:

1. A medical/dental suction nozzle holster device comprising:
   a holster component having an upper rim that is provided with at least one notch that descends downwardly into the holster component and wherein said holster component is attached to a holster mounting mechanism that further comprises a keyway slot/nub receiver opening system;
   a mounting channel component having
      (1) a front vertical plate having a face side and a rear side,
      (2) a rear vertical plate,
      (3) a horizontal ledge that interconnects the front vertical plate and the rear vertical plate and serves as a base of a bottom mounting channel region of the mounting channel component,
      (4) a top mounting channel region of the mounting channel component adapted and arranged to receive and hold an upper portion of a rail to which the mounting channel component is attached,
      (5) a bottom mounting channel region for receiving and holding a lower portion of the rail to which the mounting channel component is attached,
      (6) a right key plate that is provided with a key nub and mounted at an angle on the face side of the front vertical plate such that a bottom part of said right key plate is angled inward and downward toward a center key plate,
      (7) a center key plate that is provided with a key nub and vertically mounted on the face side of the front vertical plate, and (8) a left key plate that is provided with a key nub and mounted at an angle on the face side of the front vertical plate such that a bottom part of said left key plate is angled inward and downward toward the center key plate.

2. The medical/dental suction nozzle holster of claim 1 wherein the right key plate and the left key plate are respectively mounted at an angle from about 45° to about 65° with respect to horizontal.

3. The medical/dental suction nozzle holster of claim 1 wherein the right key plate and the left key plate are respectively mounted at an equal angle with respect to horizontal.

4. The medical/dental suction nozzle holster device of claim 1 wherein the holster component is unitary in nature owing to its being made by injection molding of a unitary holster/mounting mechanism system.

5. The medical/dental suction nozzle holster device of claim 1 wherein the mounting channel component is unitary in nature owing to its being made by injection molding of a unitary front vertical plate, horizontal ledge and rear vertical plate structure.

6. The medical/dental suction nozzle holster device of claim 1 wherein the holster mechanism further comprises a left rib, a center rib and a right rib and wherein the left rib and right rib are respectively provided with a groove for receiving a nub region in colliding contact.

7. A medical/dental suction nozzle holster device comprising:
   a holster component having an upper rim that is provided with at least one notch that descends downwardly into the holster component and wherein said holster component is attached to a holster mounting mechanism that further comprises a keyway slot/nub receiver opening system;
   a mounting channel component having
      (1) a front vertical plate having a face side and a rear side,
      (2) a rear vertical plate,
      (3) a horizontal ledge that interconnects the front vertical plate and the rear vertical plate and serves as a base of a bottom mounting channel region of the mounting channel component,
      (4) a top mounting channel region of the mounting channel component adapted and arranged to receive and hold an upper portion of a rail to which the mounting channel is attached,
      (5) a bottom mounting channel for receiving and holding a lower portion of the rail to which the mounting channel component is attached,
      (6) a right key plate that is provided with a key nub and mounted at an angle on the face side of the front vertical plate such that a bottom part of said right key plate is angled inward and downward toward a center key plate,
      (7) a center key plate that is provided with a key nub and vertically mounted on the face side of the front vertical plate,
      (8) a left key plate that is provided with a key nub and mounted at an angle on the face side of the front vertical plate such that a bottom part of said left key plate is angled inward and downward toward the center key plate, and
      (9) a finger/thumb contact device on a lower portion of the rear vertical plate.

8. The medical/dental suction nozzle holster of claim 7 wherein the right key plate and the left key plate are respectively mounted at an angle from about 45° to about 65° with respect to horizontal.

9. The medical/dental suction nozzle holster of claim 7 wherein the right key plate and the left key plate are respectively mounted at an angle of about 60° with respect to horizontal.

10. The medical/dental suction nozzle holster device of claim 7 wherein the holster component is unitary in nature owing to its being made by injection molding of a unitary holster/mounting mechanism system.

11. The medical/dental suction nozzle holster device of claim 7 wherein the mounting channel component is unitary in nature owing to its being made by injection molding of a unitary front vertical plate, horizontal ledge and rear vertical plate device structure.

12. The medical/dental suction nozzle holster device of claim 7 wherein the holster mounting mechanism further comprises a left rib, a center rib and a right rib and wherein the left rib and the right rib are respectively provided with a groove for receiving a nub region in colliding contact.

13. A medical/dental suction nozzle holster device comprising:
   an inwardly and downwardly constricted holster component having an elliptically configured top opening having an upper rim that is provided with at least one Y-shaped notch that descends downwardly into the holster component, an elliptically configured closed bottom and a holster mounting mechanism that further comprises a plate that has a left, a center and a right separation rib that attach said plate to a rear portion of the holster component and wherein said plate contains a keyway slot/nub receiver opening system;
   a mounting channel component having
      (1) a front vertical plate having a face side and a rear side,
      (2) a rear vertical plate,
      (3) a horizontal ledge that interconnects the front vertical plate and the rear vertical plate and serves as a base of a bottom mounting channel region of the mounting channel component,
      (4) a top mounting channel region of the mounting channel component adapted and arranged to receive and hold an upper portion of a rail to which the mounting channel is attached,
      (5) a bottom mounting channel for receiving and holding a lower portion of the rail to which the mounting channel component is attached,
      (6) a right key plate that is provided with a key nub and mounted at an angle on the face side of the front vertical plate such that a bottom part of said right key plate is angled inward and downward toward a center key plate,
      (7) a center key plate that is provided with a key nub and vertically mounted on the face side of the front vertical plate,
      (8) a left key plate that is provided with a nub and mounted at an angle on the face side of the front vertical plate such that a bottom part of said left key plate is angled inward toward the center key plate, and
      (9) a finger/thumb contact device in the form of a outwardly projecting nub on a bottom region of the rear vertical plate.

14. The medical/dental suction nozzle holster of claim 13 wherein the right key plate and the left key plate are respectively mounted at an angle from about 45° to about 65° with respect to horizontal.

15. The medical/dental suction nozzle holster of claim 13 wherein the right key plate and the left key plate are respectively mounted at an angle of about 60° with respect to horizontal.

16. The medical/dental suction nozzle holster device of claim 13 wherein the holster component is unitary in nature owing to its being made by injection molding of a unitary holster/mounting mechanism system.

17. The medical/dental suction nozzle holster device of claim 13 wherein the mounting channel component is unitary in nature owing to its being made by injection molding of a unitary front vertical plate, horizontal ledge and rear vertical plate structure.

18. The medical/dental suction nozzle holster device of claim 13 wherein the holster mounting mechanism further comprises a left rib, a center rib and a right rib and wherein the left rib and the right rib are respectively provided with a groove for receiving a nub region in colliding contact.

* * * * *